(12) United States Patent
Som et al.

(10) Patent No.: US 10,803,983 B2
(45) Date of Patent: Oct. 13, 2020

(54) SYSTEM AND METHOD FOR AUTO-REGULATING DRUG ADMINISTRATION FOR ACHIEVING ARTIFICIAL HOMEOSTASIS

(71) Applicant: Miraclebots, LLC, Tarpon Springs, FL (US)

(72) Inventors: Ananda Som, Tarpon Springs, FL (US); Anup Som, Berkeley, CA (US)

(73) Assignee: Miraclebots, LLC, Tarpon Springs, FL (US)

( * ) Notice: Subject to any disclaimer, the term of this patent is extended or adjusted under 35 U.S.C. 154(b) by 0 days.

(21) Appl. No.: 16/173,735

(22) Filed: Oct. 29, 2018

(65) Prior Publication Data
US 2019/0131009 A1 May 2, 2019

Related U.S. Application Data

(60) Provisional application No. 62/707,268, filed on Oct. 27, 2017.

(51) Int. Cl.
*G16H 20/17* (2018.01)
*A61B 5/00* (2006.01)
(Continued)

(52) U.S. Cl.
CPC ............. *G16H 20/17* (2018.01); *A61B 5/002* (2013.01); *A61B 5/0205* (2013.01);
(Continued)

(58) Field of Classification Search
CPC .... A61M 11/00; A61M 11/005; A61M 15/00; A61M 15/002; A61M 15/0066;
(Continued)

(56) References Cited

U.S. PATENT DOCUMENTS 5,503,156 A 4/1996 Millar
6,669,663 B1 12/2003 Thompson
(Continued)

OTHER PUBLICATIONS

Auto-Programming of Infusion Pumps conference: Learnings from an Early Adopter. BD. Date Accessed: Feb. 15, 2019. https://www.bd.com/en-us/company/video-gallery?video=1824746093001.
(Continued)

*Primary Examiner* — Valerie L Woodward
(74) *Attorney, Agent, or Firm* — Smith & Hopen, P.A.; Paul Murty (57) ABSTRACT

A system and method for auto-regulating therapeutic administration to a patient for achieving artificial homeostasis. The system includes a plurality of modules designed to create an automated therapeutic administration system. An auto-regulation module maintains a target vital level within a patient by comparing measured levels with stored target levels; a delivery module delivers an amount of a therapeutic to a patient based on instructions from the auto-regulation module, and a sensor module measures patient levels and transmits the measurements to the auto-regulation unit. The auto-regulation module compares the measured levels with the stored target levels, and, based on the comparison, instructs the delivery module to alter the amount of therapeutic administered to the patient, in an effort to match the measured levels with the target levels, thereby creating a closed feedback loop designed to achieve an artificial homeostasis for a patient.

8 Claims, 7 Drawing Sheets

(51) Int. Cl.

| | | |
|---|---|---|
| | *A61M 5/172* | (2006.01) |
| | *G16H 10/60* | (2018.01) |
| | *A61B 5/0205* | (2006.01) |
| | *G16H 20/40* | (2018.01) |
| | *G16H 40/63* | (2018.01) |
| | *G16H 20/10* | (2018.01) |
| | *A61M 16/00* | (2006.01) |
| | *A61M 16/10* | (2006.01) |
| | *G16H 50/30* | (2018.01) |
| | *A61B 5/145* | (2006.01) |
| | *A61B 5/1455* | (2006.01) |
| | *A61B 5/0215* | (2006.01) |
| | *A61B 5/0408* | (2006.01) |
| | *A61B 5/024* | (2006.01) |
| | *A61B 5/0478* | (2006.01) |
| | *A61B 5/0245* | (2006.01) |
| | *A61B 5/08* | (2006.01) |

(52) U.S. Cl.
CPC ........ *A61B 5/02055* (2013.01); *A61B 5/4839* (2013.01); *A61M 5/1723* (2013.01); *A61M 16/024* (2017.08); *A61M 16/1005* (2014.02); *G16H 10/60* (2018.01); *G16H 20/10* (2018.01); *G16H 20/40* (2018.01); *G16H 40/63* (2018.01); *A61B 5/0215* (2013.01); *A61B 5/0245* (2013.01); *A61B 5/02416* (2013.01); *A61B 5/0408* (2013.01); *A61B 5/0478* (2013.01); *A61B 5/082* (2013.01); *A61B 5/14517* (2013.01); *A61B 5/14532* (2013.01); *A61B 5/14539* (2013.01); *A61B 5/14551* (2013.01); *A61B 5/686* (2013.01); *A61B 5/6833* (2013.01); *A61M 2230/06* (2013.01); *A61M 2230/201* (2013.01); *A61M 2230/205* (2013.01); *A61M 2230/208* (2013.01); *A61M 2230/30* (2013.01); *G16H 50/30* (2018.01)

(58) Field of Classification Search
CPC .......... A61M 15/0085; A61M 16/0003; A61M 16/022–026; A61M 2016/1025; A61M 2230/205; A61M 2230/435; A61M 16/1005; G16H 10/60; G16H 20/17; G16H 20/40; G16H 40/63
See application file for complete search history.

(56) References Cited

U.S. PATENT DOCUMENTS

| | | | |
|---|---|---|---|
| 7,128,714 B1 | 10/2006 | Antonelli | |
| 7,785,313 B2 | 8/2010 | Mastrototaro | |
| 8,062,249 B2 | 11/2011 | Wilinska et al. | |
| 8,066,694 B2 | 11/2011 | Wagener | |
| 2008/0078382 A1* | 4/2008 | LeMahieu | A61M 16/107 128/200.24 |
| 2010/0224192 A1* | 9/2010 | Dixon | A61B 5/0205 128/204.23 |
| 2013/0032147 A1* | 2/2013 | Robinson | A61M 16/0051 128/204.18 |
| 2013/0239961 A1* | 9/2013 | Ross, Jr. | A61M 16/10 128/202.22 |
| 2014/0202455 A1* | 7/2014 | Garde | A61B 5/4836 128/200.14 |
| 2016/0144146 A1* | 5/2016 | Huddart | A61M 16/0683 128/206.21 |
| 2016/0199593 A1* | 7/2016 | Morrison | A61M 11/005 128/200.16 |
| 2017/0150939 A1* | 6/2017 | Shah | A61B 6/548 |
| 2017/0182277 A1* | 6/2017 | Niklewski | A61M 16/0051 |
| 2018/0099109 A1* | 4/2018 | Kinsky | A61M 16/024 |
| 2019/0038854 A1* | 2/2019 | Fuchs | A61M 15/009 |

OTHER PUBLICATIONS

11 Elite Nanomite Programmable Remote Head Syringe Pump by Harva. Medline. Date Accessed: Feb. 15, 2019. https://www.medline.com/product/11-Elite-Nanomite-Programmable-Remote-Head-Syringe-Pump-by-Harva/Blood-Collection-Sets/Z05-PF96547?question=digital+interface&index=P24&indexCount=24.

Pressure Control Inside a Microfluidic System. Elveflow Plug & Play Micofluidics. Date Accessed: Feb. 15, 2019. https://www.elveflow.com/microfluidic-tutorials/microfluidic-applications/pressure-sensor-feedback-loop/.

MiniMed™ 670G Insulin Pump System. Medtronic. Date Accessed: Feb. 15, 2019. https://www.medtronicdiabetes.com/products/minimed-670g-insulin-pump-system.

Mobility Solutions: IntelliVue Mobile Caregiver. Phillips. Date Accessed: Feb. 15, 2019. https://www.usa.philips.com/healthcare/product/HCNOCTN197/intellivue-mobile-caregiver-mobile-app-for-patient-monitoring-data.

\* cited by examiner

SYSTEM AND METHOD FOR AUTO-REGULATING DRUG ADMINISTRATION FOR ACHIEVING ARTIFICIAL HOMEOSTASIS

CROSS-REFERENCE TO RELATED APPLICATIONS

This nonprovisional application is a continuation of and claims priority to provisional application No. 62/707,268, entitled "System and Method for Auto-Regulating Drug Administration for Achieving Artificial Homeostasis," filed on Oct. 27, 2017, by the same inventors.

BACKGROUND OF THE INVENTION

1. Field of the Invention

This invention relates, generally, to adaptive drug delivery systems. More specifically, it relates to a system and method for auto-regulating the administration of titratable fluids, medications, gases, and other substances for the treatment of patients.

2. Brief Description of the Prior Art

Living organisms have a tendency to maintain a stable, consistent target state, otherwise known as homeostasis. In order to maintain homeostasis, living beings have associated bodily functions that include precise feedback loops designed to automate the process, with the target being placing the living beings in a consistent, healthy state. The feedback loops involve certain mechanisms within the body that are designed to react to changes in the equilibrium parameters of a particular body, and to negate the change in equilibrium. The goal of homeostasis and the associated bodily functions designed to maintain homeostasis is to ensure and maintain internal balances. Some examples of homeostatic monitoring and control mechanisms include temperature homeostasis, circadian homeostasis, metabolic homeostasis, endocrine homeostasis, neural homeostasis, respiratory homeostasis, and fluid homeostasis.

In many disease states, such auto-regulating mechanisms breakdown, causing imbalances within the affected body. Maintenance of homeostasis is essential for the survival of all living beings. Accordingly, when a homeostatic imbalance occurs, frequent monitoring of the different parameters associated with the affected body is required for effective treatment. If the homeostatic imbalance is monitored and altered artificially, such as through medicinal treatment to attempt to recreate a balance, the process can be referred to as someostasis (a new pathophysiological state of health achieved by any artificial methods of maintaining homeostasis).

Various devices are available to detect and monitor health parameters. Such monitoring devices may present numerical values indicating the measured health parameter levels; however, these numerical values need to be interpreted by a medical expert to determine a deviation from the healthy, homeostatic state of the subject, and subsequently decide the next course of action. For example, currently available bedside biosensors can measure numerous vital signs, such as blood pressure, heart rate, oxygen saturations, temperature, and blood glucose. In addition, blood samples can be obtained from a patient and sent to a laboratory for chemistry analysis for sodium, potassium, bicarbonate, and pH levels, with the measured data being reported, either via paper or electronic records, to one or more medical care providers or to a hospital's electronic health record (EHR).

As such, the present state of patient care includes measuring vital signs of the patient, manually drawing blood for chemical analyses, and entering the results into the hospital's EHR, either manually or electronically. Since these processes are typically completed by different individuals, there is often a time delay involved in the processes. In addition, after the basic test results are obtained, a physician subsequently interprets the clinical data to determine the specific initial treatment that is required, such as an IV fluid and flow rate. Often, assisting personnel, such as nurses, manually program an infusion pump to deliver the fluid or drug to the patient. Some modern smart pumps can be programmed via the EHR system or via a health care professional to provide for remote, manual control over flow rates by monitoring biosensors connected to the patient. For example, the current state of the art for parenteral fluid and drug delivery systems are semi-programmable pumps with clinicians entering the flow rates and monitoring vital signs or laboratory results at intermittent intervals to achieve desired goals. As such, management of patient vital levels include labor intensive processes, and, especially in an intensive care unit (ICU) setting, may require a medical professional to stay at the bedside of a critically ill patient to provide one-on-one care for extended periods of time until favorable outcomes are achieved. At the present time, the output from the biosensors is not automatically communicated back to a decision support process or delivery pump that can automatically regulate (or auto-regulate) the future flow rate to achieve desired goals.

Accordingly, what is needed is a device and method of achieving automatic regulation of patient homeostasis via monitoring patient health parameter levels, using an automated feedback loop to deliver treatments necessary to maintain homeostasis based on the measured levels. Such a device and method would increase the efficiency of maintaining homeostatic balance within a patient, as well as the efficiency of healthcare professionals, since certain aspects of their responsibilities would be performed by a device. As such, such a device and method would reduce costs and resources associated with maintaining homeostatic balance within a patient. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an autoregulation system including wireless communications and drug delivery devices, that monitors selected patient vital levels and automatically achieves a target level, is now met by a new, useful, and nonobvious invention.

The novel system includes an auto-regulation module in electronic communication with a delivery module and a sensor module. The auto-regulation module is an electronic device including a memory, a signal transmitter, and a signal receiver, with the memory designed to store a target vital level for a patient. The delivery module is couplable to the patient and includes a signal receiver and a delivery device. The delivery module signal receiver receives a signal from the auto-regulation module, the signal providing an instruction to deliver an amount of a therapeutic to the patient via the delivery device. The amount of the therapeutic administered to the patient is selected to alter a measured vital level for the patient. The sensor module is also couplable to the patient and includes a signal transmitter and a sensing component. The sensing component is adapted to detect the measured vital level for the patient, and the signal transmitter is adapted to send the measured vital level to the auto-regulation signal receiver. The system creates a closed loop in which the auto-regulation module receives the measured vital level from the sensor module, compares the measured vital level to the target vital level in the memory, and updates the signal sent to the delivery module signal receiver to update the amount of the therapeutic adapted to be administered to the patient via the delivery device.

In an embodiment of the system, the target vital level is an oxygen saturation level for the patient. Accordingly, the system includes a cannula coupled to the patient, with the cannula being a part of the delivery module and being adapted to supply oxygen to the patient to alter the patient's oxygen saturation level. The sensing component in this embodiment is a pulse oximeter that is adapted to measure the patient's oxygen saturation level, the pulse oximeter being electronically coupled to the sensor module signal transmitter which transmits the measured oxygen saturation level to the auto-regulation module.

In an embodiment of the system, the target vital level is a blood pressure level for the patient. Accordingly, the system includes a blood pressure monitor coupled to the patient, with the blood pressure monitor being a part of the sensor module and being designed to measure the patient's blood pressure. The system also includes an intravenous catheter coupled to the patient, with the intravenous catheter being a part of the delivery module and being adapted to supply the amount of the therapeutic to the patient to match the measured blood pressure with the target blood pressure. The therapeutic is Nicardipine, and the auto-regulation module determines the amount of the Nicardipine necessary to equate the measured blood pressure with the target blood pressure.

An embodiment of the invention includes an electrical device including an electronic health record, with the electronic health record being in communication with the auto-regulation module, such that the auto-regulation module can send and receive patient data to and from the electronic health record. The auto-regulation module may be a mobile application designed to be loaded on a storage medium of a mobile electronic device. As such, the auto-regulation module is in wireless communication with the delivery module and the sensor module, such that the measured vital level, target vital level, and amount of the therapeutic can be monitored via the mobile electronic device. The mobile electronic device also includes a notification component, such that the measured vital level, target vital level, and amount of the therapeutic can be communicated to other mobile electronic devices, such that a plurality of care providers can be alerted to the patient's status.

The novel method includes the steps of detecting a vital level of a patient through a sensor module; receiving a feedback signal from the sensor module at an auto-regulation module; and comparing the detected vital level of the patient with a target vital level. If the detected vital level and target vital level are not equal, the method includes the step of instructing a delivery module in electronic communication with the auto-regulation module to deliver an amount of a therapeutic to the patient to alter the detected vital level to equate the detected vital level with the target vital level. If the detected vital level and target vital level are equal, instructing the delivery module to maintain the detected vital level to achieve an artificial homeostasis. The system may continuously detect the patient's vital level via the sensor module at predetermined intervals and, may continuously transmit the detected vital level to the auto-regulation module, thereby creating a continuously-repeating closed feedback loop to monitor the patient's status and maintain the artificial homeostasis. Moreover, the system may include the monitoring of a plurality of vital levels near-simultaneously through a plurality of sensing components within the sensor module. As such, the auto-regulation module can monitor and maintain the artificial homeostasis for each of the plurality of vital levels.

An object of the invention is to provide a device, system, and method for the automatic regulation of therapeutic administration to achieve artificial homeostasis.

Another object of the invention is to reduce the need for human intervention in the administration of therapeutics, such as titratable fluids, medications, and gases, to maintain homeostatic balances in treated patients, thereby reducing the cost and time associated with such human intervention, as well as increasing accuracy and efficiency of treatment.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a system and method for auto-regulating drug administration for achieving artificial homeostasis. The system includes a plurality of modules designed to create an automated drug administration system, such as an auto-regulation module that maintains a target vital level within a patient, a patient-integration delivery module that receives instructions from the auto-regulation module and delivers a determined amount of a drug or compound to a patient, and a sensor module that monitors selected vital data and transmits measured data to the auto-regulation unit. The method involves closely monitoring a patient's vital levels, such as pulse, blood pressure, $O_2$ levels, and other vital levels; monitoring the patient's lab values (such as the level of certain compounds administered to and residing within the patient's body); and feeding the output from the vital signs or lab values to the auto-regulation module. The auto-regulation module compares the desired parameter values with the actual values obtained and, based on the comparison, instructs the delivery module to administer a selected amount of one or more compounds to achieve a target level of the monitored parameter. Normal ranges of the measured parameter may be derived from a patient's previous values recorded in the EHR, or may be derived from a default setting per predetermined normal parameters and clinical guidelines. Through the system and method, an automated feedback loop is created, wherein the interaction between the modules provides for an automated process of monitoring patient vital signs, determining a target level for one or more vital levels, instructing a delivery device to alter a measured level to equal the target level, and repeating the steps to create an artificial homeostasis within the patient.

Figure 1A:
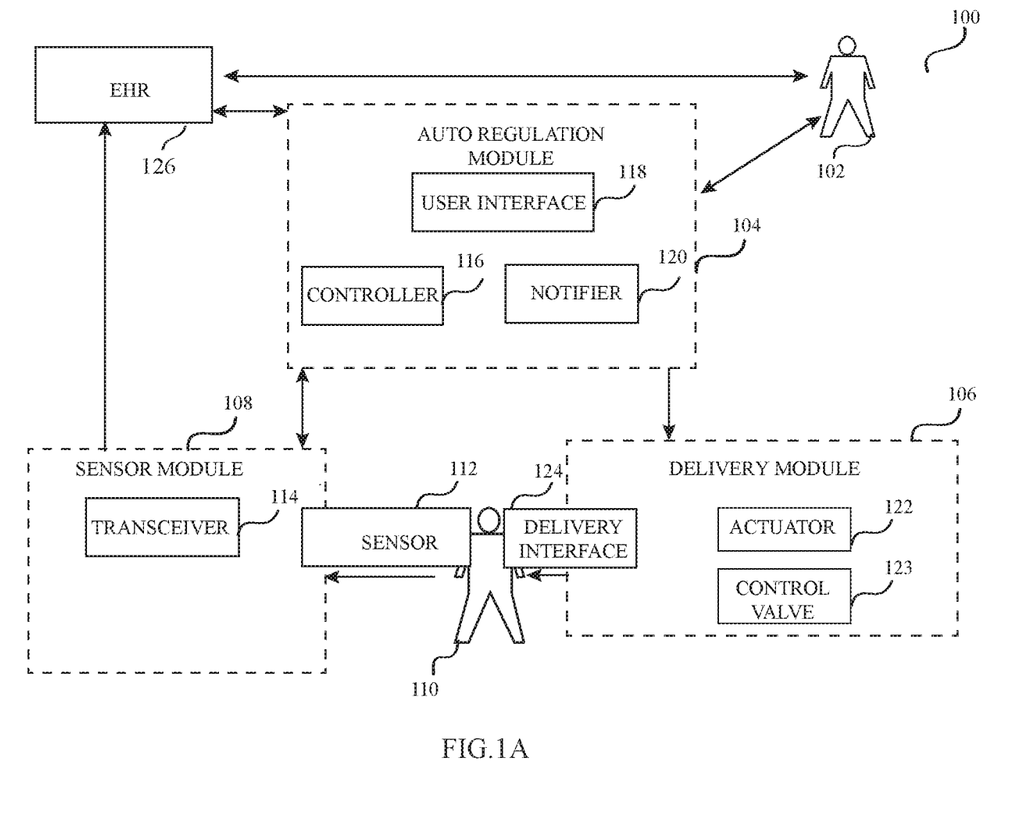
FIG. 1A depicts an automated regulation system designed to monitor and alter a patient's vital levels to achieve an artificial homeostasis by utilizing an automated feedback loop, in accordance with an embodiment of the present invention.

As shown in FIG. 1A, system 100 includes auto-regulation module 104, delivery module 106, and sensor module 108. Auto-regulation module 104 is an electronic device that is in communication with each of delivery module 106 and sensor module 108. The communication may be accomplished through a physical, wired connection, or may be a wireless connection, with transmissions sent and received by auto-regulation module 104 via RF waves from an antenna. The electronic device of auto-regulation module 104 can be a component of a computing device, such as an API (application program interface), or may be an independent computing device, such as a cellular device, tablet, hand-held device, laptop, desktop computer, or other device capable of wired or wireless communications. Auto-regulation module 104 includes user interface 118, through which a user can interact with auto-regulation module 104. User interface 118 can be a traditional screen in combination with an interactive device, such as a mouse or keyboard, or can be a touchscreen on a mobile device or laptop. User interface 118 also includes a graphical user interface, or GUI, that provides an interactive platform through which a user can easily interact with auto-regulation module 104. Moreover, auto-regulation module 104 includes controller 116 in communication with user interface 118. Controller 116 may be a touchscreen integrated into the computing device and may be interactable via user interface 118; in alternative embodiments, controller 116 may be a mouse, keyboard, or other interactive device through which a care provider (denoted by reference numeral 102) can send instructions to deliver module 106, which will be discussed in greater detail below. Auto-regulation module 104 further includes notifier 120, which is in communication with sensor module 108, such as via wireless communications through RF signals. Notifier 120 is designed to receive signals from sensor module 108, and provide a notification to care provider 102 regarding a selected one or more vital level of patient 110. Sensor module 108 will also be discussed in greater detail below.

Delivery module 106 includes a patient interaction component, such as delivery interface 124, as well as a signal-receiving component that is in communication with auto-regulation module 104. Similar to auto-regulation module 104, delivery module 106 may be an electronic device capable of wired or wireless communications to auto-regulation module 104. Specifically, delivery module 106 is capable of receiving instructions from auto-regulation module 104, such as via RF transmissions received by an antenna. The signal-receiving component is designed to receive instructions from auto-regulation module 104, and instruct delivery interface 124 to perform a function based on the instructions received from auto-regulation module 104.

In an embodiment, as shown in FIG. 1A, delivery module 106 includes flow actuator 122 and flow control valve 123, which are in communication with delivery interface 124. Other components of delivery module 106 that may be included in certain embodiments are a pump and a power source, which can be external through a plug or internal through an integrated battery. The components of delivery module 106 are in communication with one another and are designed to interact with a patient via delivery interface 124. For example, actuator 122 is a mechanical device that controls the delivery of a therapeutic from delivery module 106 when delivery module 106 receives instructions from auto-regulation module 104. Examples of an actuator include a micro-electric-mechanical system (MEMS) device or a piezoelectric actuator. Actuator 122 regulates and controls flow control valve 123 to vary the amount of a therapeutic flowing through flow control valve 123 to delivery interface 124. For example, if the therapeutic is a fluid drug, actuator 122 controls the amount of fluid flowing to delivery interface 124 and ultimately to the patient. In an embodiment, delivery module 106 includes a reservoir to store an amount of therapeutic therein, with the reservoir in communication with actuator, such that delivery module 106 can draw fluid from the reservoir and deliver the therapeutic to the patient. Alternatively, delivery module 106 may be in communication with an external reservoir or other storage medium. If a pump is included, together with a power source, the power source supplies power to the pump, which actively drives therapeutics to delivery interface 124, thereby pushing the therapeutics to patient 110.

Delivery interface 124 is designed to interact with a patient, and varies in design based on the ultimate therapeutic need. In an embodiment, delivery interface 124 is a nebulizer, inhaler, mask, nasal cannula, or other device designed to deliver a gaseous fluid to a patient. In an alternative embodiment, delivery interface 124 is a catheter, such as an intravenous, arterial, subcutaneous, enteral, parenteral, intrathecal, visceral, or intra-cavitary catheter. Still other delivery interfaces can include tracheostomy or endotracheal tubes to be used with ventilator patients. Regardless of the design, delivery interface 124 is designed to deliver one or more selected therapeutics to a patient to achieve homeostasis.

Sensor module 108 includes one or more sensors 112 and transceiver 114. Sensors 112 are directly or indirectly coupled to patient 110 to detect and store values of the patient's vital levels. For example, sensors 112 may include biosensors placed on the patient's body to detect blood pressure or heart rate; pulse oximeters placed on the patient's fingertips to detect oxygen saturation or heart rate; electrodes placed on the patient's body to detect heart rate or heart rhythm data, such as EKG electrodes; or electrodes placed on the patient's head to detect brain activity data, such as EEG electrodes. While the above examples of sensors 112 are commonly associated with inpatient or outpatient applications, it is contemplated that sensors 112 may be used in a mobile environment for patients in a home setting, or otherwise outside of a clinical facility. For example, sensors 112 may be wearable biosensors to detect various patient vital levels, such as contact lenses, skin patches, sweat and tear sensors, breath analyzers, or other wearable devices; buccal salivary sensors; subcutaneous or submucosal implants; microassay chips; body fluid chemistry sensors, such as blood or urine sensors; or combinations of the above to detect patient vital signs or chemistry values, such as levels of glucose, sodium, potassium, specific gravity, osmolality, pH, bicarbonate, oxygen, $CO_2$, and other parameters. Sensors 112 may be directly coupled to patient 110 via the sensors discussed above, a pacemaker, a defibrillator, an implanted port, an IV or intra-arterial catheter, and the like; or may be indirectly coupled to patient 110 via a patient's hospital bed, a telemetry apparatus, peak expiratory flow meter (PEFR) to obtain peak flows, or similar device external to patient 110. The frequency of vital sign detection by sensors 112 may be predetermined, scheduled, and automated; or on-demand via a medical provider interacting with auto-regulation module 104.

Transceiver 114 is designed to send signals to auto-regulation module 104 via RF waves from an antenna, such that auto-regulation module 104 receives patient data for the purpose of analyzing the data, comparing the data to a target set of data, and instructing delivery module 106 to alter an amount of a therapeutic being administered to patient 110. As such, the components of system 100 work together to detect the patient's vital levels, compare the data to a target level, and alter therapeutics until the detected patient data substantially matches a target level, thereby creating an artificial homeostasis aided by a therapeutic.

Figure 1B:
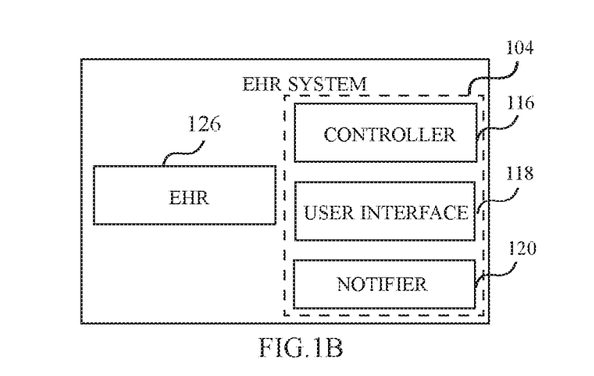
FIG. 1B depicts components of the automated regulation system of FIG. 1A, in particular the EHR which interacts with the system, in accordance with an embodiment of the present invention.
Figure 1C:
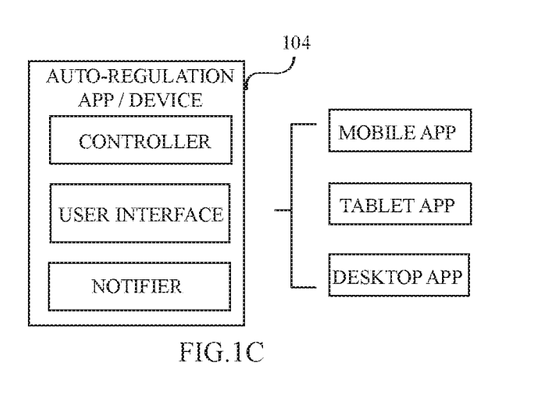
FIG. 1C depicts components of the automated regulation system of FIG. 1A, in particular the auto-regulation module, in accordance with an embodiment of the present invention.

FIGS. 1B-1C depict detailed views of embodiments of system 100 as discussed in detail above. For example, FIG. 1B depicts an embodiment of system 100 in which auto-regulation module 104 is integrated within a facility's EHR 126, as opposed to being disposed on an electronic device external to the EHR 126. FIG. 1C depicts various external electronic devices on which auto-regulation module 104 may be disposed, such as an application designed to run on a mobile electronic device, a tablet, or a desktop computing device.

Figure 1D:
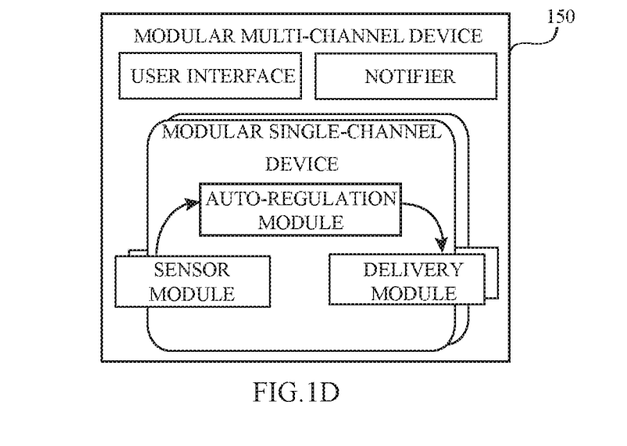
FIG. 1D depicts an embodiment of the automated regulation system of FIG. 1A that utilizes a modular multi-channel device, in accordance with an embodiment of the present invention.
Figure 1E:
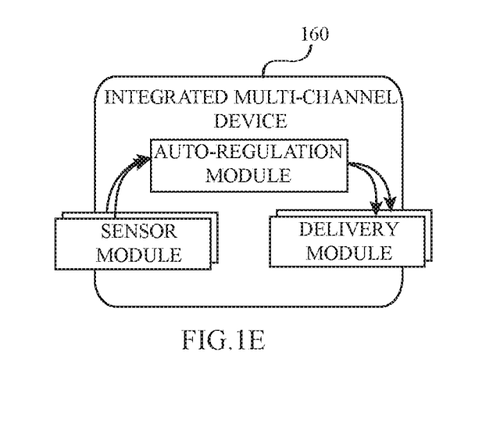
FIG. 1E depicts an embodiment of the automated regulation system of FIG. 1A that utilizes an integrated multi-channel device, in accordance with an embodiment of the present invention.

FIG. 1D depicts an embodiment of system 100 including modular multi-channel device 150. In the embodiment of FIG. 1D, each of the modules are separate from each other, while functioning together to create system 100—said another way, the modules are disposed on electronic devices in communication with one another, but separate from one another, as shown in FIG. 1D. Similarly, FIG. 1E depicts an embodiment of system 100 including integrated multi-channel device 160. In the embodiment of FIG. 1E, each of the modules is integrated on a singular device 160 in which the modules are in communication with one another, whether wireless or wired, while being disposed on the same device.

Figure 2:
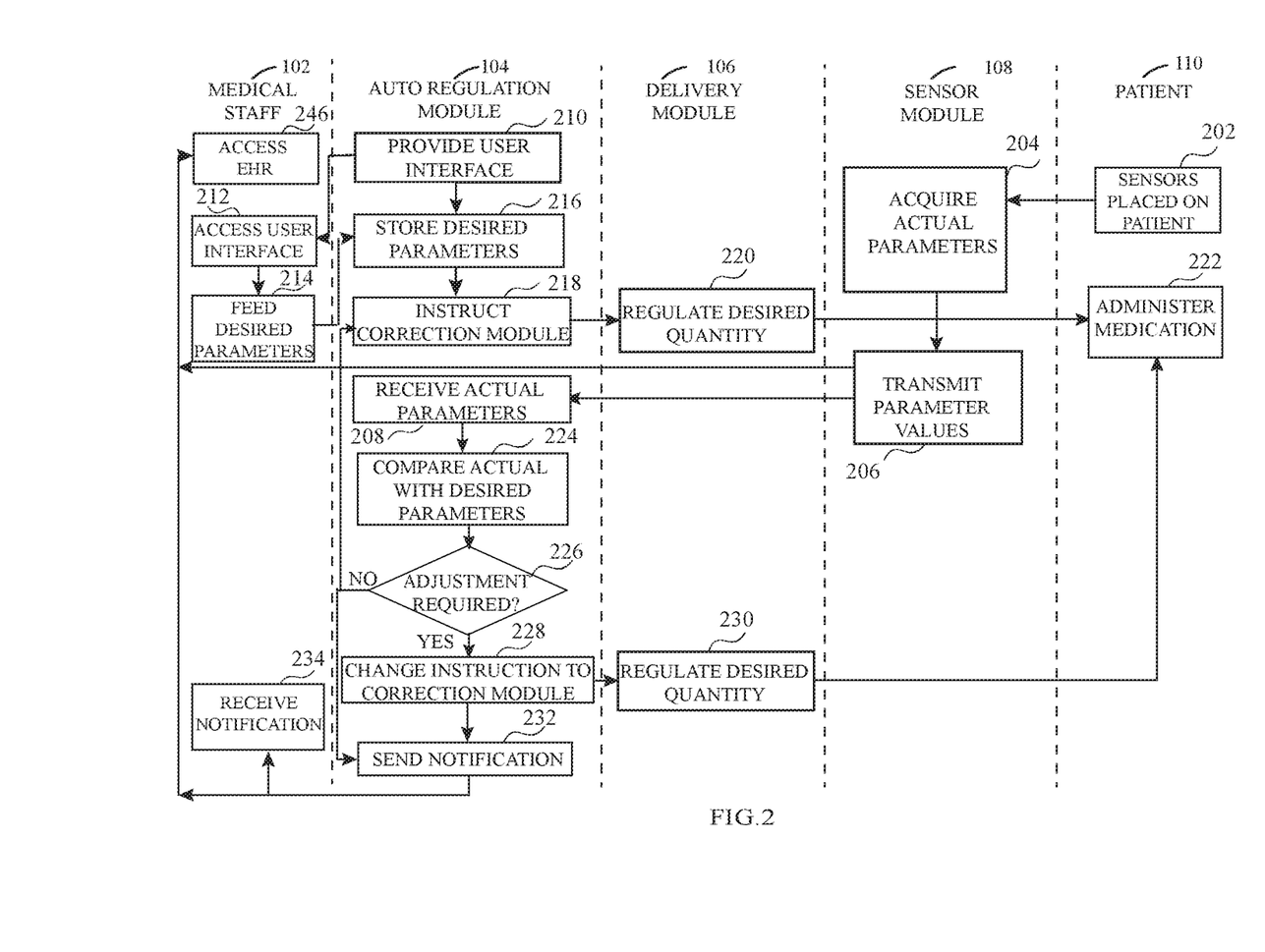
FIG. 2 is a process flow diagram depicting a method of automatically regulating a patient's vital levels, in accordance with an embodiment of the present invention.

FIG. 2 depicts a method of using system 100 to monitor vital levels of patient 110. The method is depicted as a process flow diagram utilizing the components discussed in detail above, particularly auto-regulation module 104, delivery module 106, and sensor module 108. As shown in FIG. 2, in combination with FIGS. 1A-1C in particular, system 100 enables the auto-regulating administration of titratable therapeutics for the treatment of patient 110 to achieve artificial homeostasis, or someostasis. As shown in step 202 of FIG. 2, one or more sensors 112 can be used to acquire data related to various physiological parameters, such as vital signs, of patient 110 being treated for homeostatic imbalance. In some embodiments, as in step 204, sensor module 108 can also acquire different laboratory values apart from the data provided by the sensors 112. Sensor module 108 transmits the acquired actual values to auto-regulation module 104 through transceiver 114, as shown in step 206. In a preferred embodiment, sensor module 108 also transmits the acquired actual values to EHR 126.

As shown in step 210 of FIG. 2, auto-regulation module 104 provides user interface 118, as discussed in detail above. In an embodiment, care provider 102 (which may be a medical staff member, such as a doctor, a paramedic, a nurse, and other medical professionals, or may be a lay person in other embodiments) can access the EHR 126 in step 246 to study the health record of patient 110. In some embodiments, the EHR 126 is communicatively connected to auto-regulation module 104, such that the health records of patient 110 can be accessed directly through user interface 118 of auto-regulation module 104. In some embodiments, the EHR 126 is completely replaced by the auto-regulation module 104 with all the functionalities of the EHR 126 being provided by auto-regulation module 104 with or without interacting with an Artificial Intelligence (AI) machine.

Care provider 102 can access the user interface 118, as shown in step 212, and set the desired parameter values, as shown in step 214, required to correct a homeostatic imbalance in patient 110 being treated. For example, a physician can evaluate patient 110 and enter orders into the EHR 126 for a nurse regarding: the diagnosis of patient 110; the type of therapeutics required to treat patient 110; an initial flow rate of the therapeutics; and a desired parameter value for patient 110, such that patient 110 receives treatment. Controller 116 also can estimate or suggest initial, starting values based on default levels per established clinical guidelines, or based on patient-specific data, such as age, weight, renal function, or previous baseline levels for patient 110 that may be stored in the EHR 126. Auto-regulation module 104 stores the desired parameter values in a memory unit (which is not shown in the drawings, but is a component of many electronic devices that would be understood by a person of ordinary skill in the art) as in step 216. The memory unit can be part of the system 100 or it can be cloud-based, or integrated into an AI component. Based on the desired values, controller 116 instructs, as shown in step 218, delivery module 106 to regulate administration of the therapeutic into patient 110. Delivery module 106, by using actuator 122 and control valve 123, regulates the flow of the therapeutics, as shown in step 220, delivered through delivery interface 124 to patient 110, which is shown in step 222.

Sensor module 108 monitors patient 110 to acquire the actual values of the physiological parameters of patient 110, such as on a continuous basis in real-time, or at predetermined intervals that can be manually set by care provider 102 or automatically set by controller 116. The acquired parameters are continuously compared with the target parameters by controller 116, as shown in step 224. If controller 116 finds any anomalies between the target parameters and the acquired parameters, controller 116 decides, as shown in step 226, to increase or decrease the amount of the therapeutic being administered to patient 110. If, however, controller 116 determines that the acquired parameters are within a target range of target parameters (i.e., ±5%, depending on the importance of equality between the target parameters and the acquired parameters), then an artificial homeostasis has been achieved, and no change in the therapeutic administration is required at that moment. As used herein, the term "equal" means within a tolerance value of ±5%, such that if an acquired parameter is within 5% of a target parameter, the parameters can be said to be equal for the purposes of achieving an artificial homeostasis.

The amount of therapeutic is altered by controller 116 instructing, as shown in step 228, delivery module 106 to alter the therapeutic supply to patient 110, such as by increasing or decreasing the amount of therapeutic given to patient 110. Actuator 122 regulates control valve 123 based on a signal received from auto-regulation module 104, as shown in step 230. Thus, a positive or negative feedback loop can be created for achieving artificial homeostasis, or someostasis, by using system 100 of the present invention. Moreover, notifier 120 of auto-regulation module 104 can be configured to send alerts to one or more users of system 100, such as shown in step 232. In an embodiment of the invention, notifications and records of parameters being monitored are sent both to the EHR 126 and to auto-regulation module 104. One or more care providers 102 can receive the alerts through user interface 118 of auto-regulation module 104, or on a separate mobile computing device, as shown in step 234.

Figure 3:
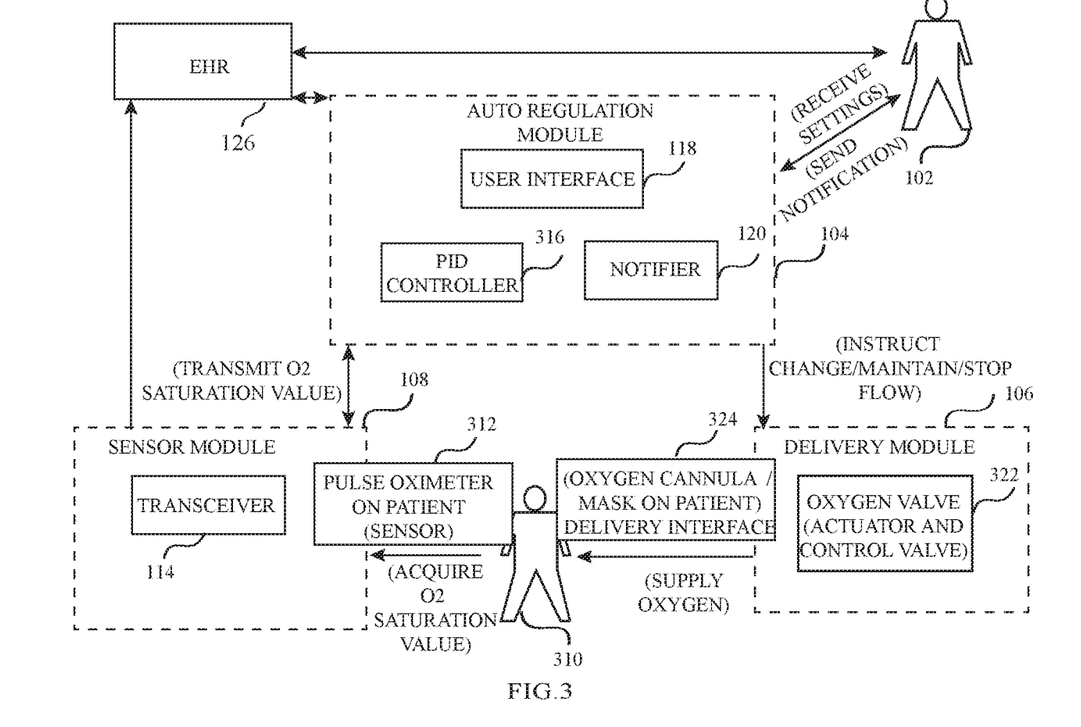
FIG. 3 depicts an automated regulation system designed to monitor and alter a patient's vital levels, specifically the patient's $O_2$ saturation levels, to achieve an artificial homeostasis by creating an automated feedback loop, in accordance with an embodiment of the present invention.

FIG. 3 depicts an embodiment of system 100 utilized to treat patient 310 having hypoxia or shortness of breath. While many of the components of system 100 are present in the embodiment shown in FIG. 3, such as autoregulation module 104, delivery module 106, and sensor module 108, specific examples of components of system 100 are shown in greater detail in FIG. 3. For example, a specific example of a delivery device is shown in delivery module 106, which includes oxygen valve 322 (comprising an actuator and a control valve, similar to the delivery module discussed in detail above) and oxygen cannula 324 (similar to delivery interface 124 discussed above). Similarly, sensor module 108 includes pulse oximeter 312 that acquires an $O_2$ saturation level of patient 310 having hypoxia. Pulse oximeter 312 is a specific example of a type of sensor 112, as discussed above. The controller of auto-regulation module 104 is also shown as PID (proportional-integral-differential) controller 316, which, again, is a specific example of a type of controller 116 as discussed above.

Figure 4:
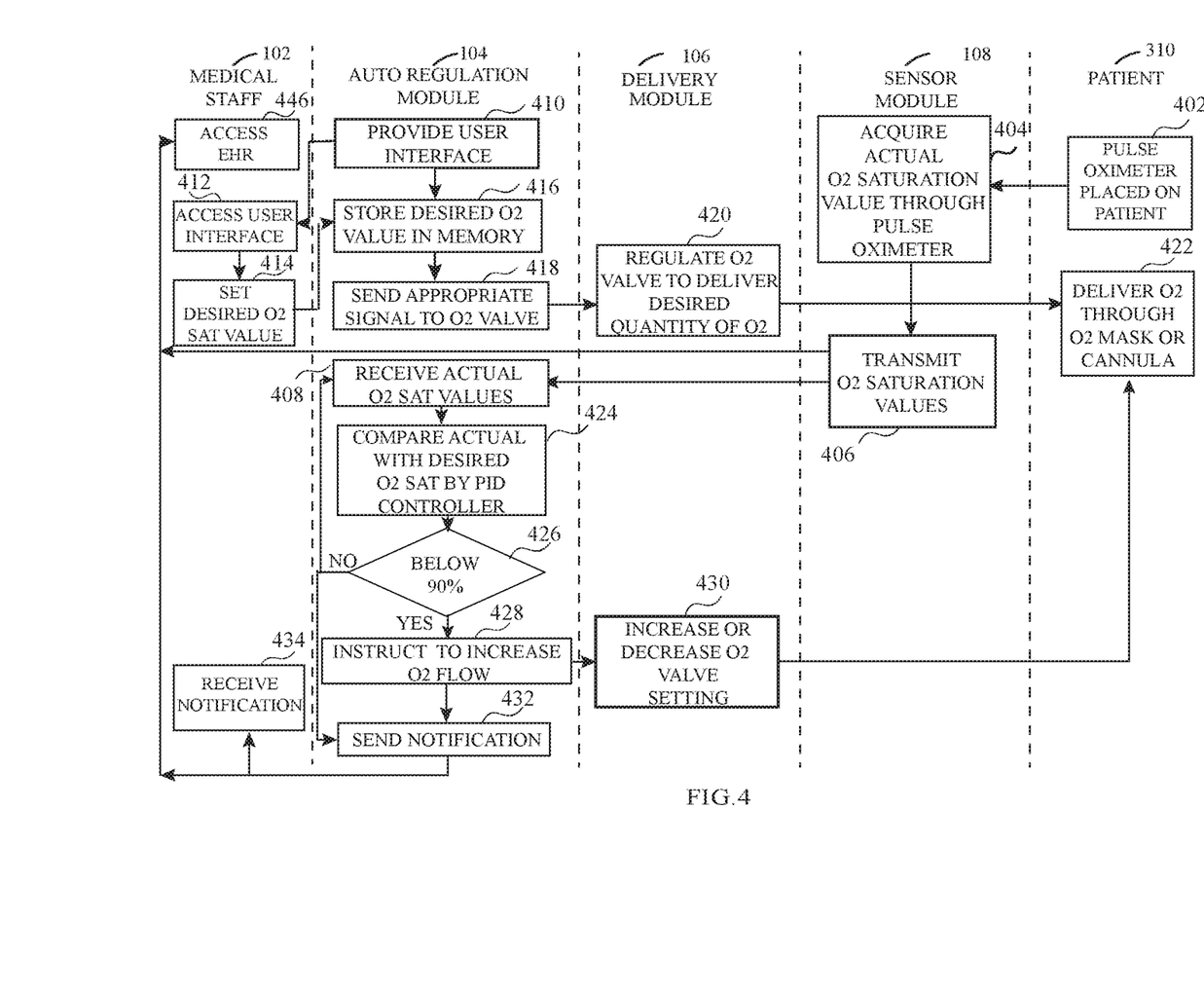
FIG. 4 depicts a process flow diagram depicting a method of automatically regulating a patient's $O_2$ saturation levels, in accordance with an embodiment of the present invention.

FIG. 4 depicts a process flow diagram of a method of treating patient 310 having hypoxia, and is discussed in conjunction with FIG. 3. Pulse oximeter 312 is used on patient 310 as in step 402 to acquire oxygen saturation ($O_2$ sat) value by sensor module 108, as shown in step 404. Transceiver 114 of sensor module 108 sends the $O_2$ saturation value to the auto-regulation module 104, as shown in step 406. Care provider 102 treating patient 310 can access the EHR 126, as shown in step 446, to read the medical records of the patient 310, and also access user interface 118 of auto-regulation module 104, as provided in step 410 and as accessed in step 412. Care provider 102 can enter the target oxygen saturation value which is to be achieved for patient 310, with this value being stored in auto-regulation module 104, as shown in step 416.

As shown in step 422, oxygen cannula 324 administers or facilitates the administration of oxygen, a therapeutic, to patient 310. Auto-regulation module 104 instructs delivery module 106 to regulate the flow of oxygen administered to patient 310, as shown in step 418, in line with the desired value set by care provider 102, or determined by an AI component integrated within the EHR 126 or auto-regulation module 104, or in communication with the EHR 126 or auto-regulation module 104. As shown in step 420, oxygen valve 322 of delivery module 106 is adjusted to regulate the flow of oxygen to patient 310.

Upon receiving the actual, or measured, $O_2$ saturation level for patient 310 via pulse oximeter 312 (which functions similarly to sensor 112, discussed above) during step 408, PID controller 116, during step 424, compares the actual levels with the target levels. PID controller 316 continuously calculates an error value as the difference between the target levels and the measured levels. PID controller 316 attempts to minimize the error over time by adjustment of a control variable, such as the position of control valve 322. If PID controller 316 finds, as shown in step 426, that the oxygen saturation level in patient 310 measured by pulse oximeter 312 is above, for example, 90%, then PID controller 316 instructs delivery module 106 to continue the oxygen supply at a steady rate and, if the oxygen saturation level is found to be below, for example, 90%, PID controller 316 instructs delivery module 106 to increase the oxygen flow rate to patient 310, as shown in step 428. The adjustment of oxygen flow rate may be accomplished, as shown in step 430, by changing the settings or position of control valve 322 in delivery module 106. Thus, as discussed above, the present invention provides a closed loop control system, because the process of reading sensors to provide constant feedback and calculating the desired actuator output is repeated continuously and at a fixed loop rate. Accordingly, proper adjustment of oxygen supply from, for example, a central wall supply, ventilator, portable concentrator, or BiPAP/CPAP (bilevel positive airway pressure/continuous positive airway pressure) machine to patient 310 occurs automatically to achieve a homeostatic balance. The system also sends notification, as shown in step 432, and updates the EHR 126 with the latest results in real-time. The notifications can be sent to one or more other interested persons apart from care provider 102, as shown in step 434.

Figure 5:
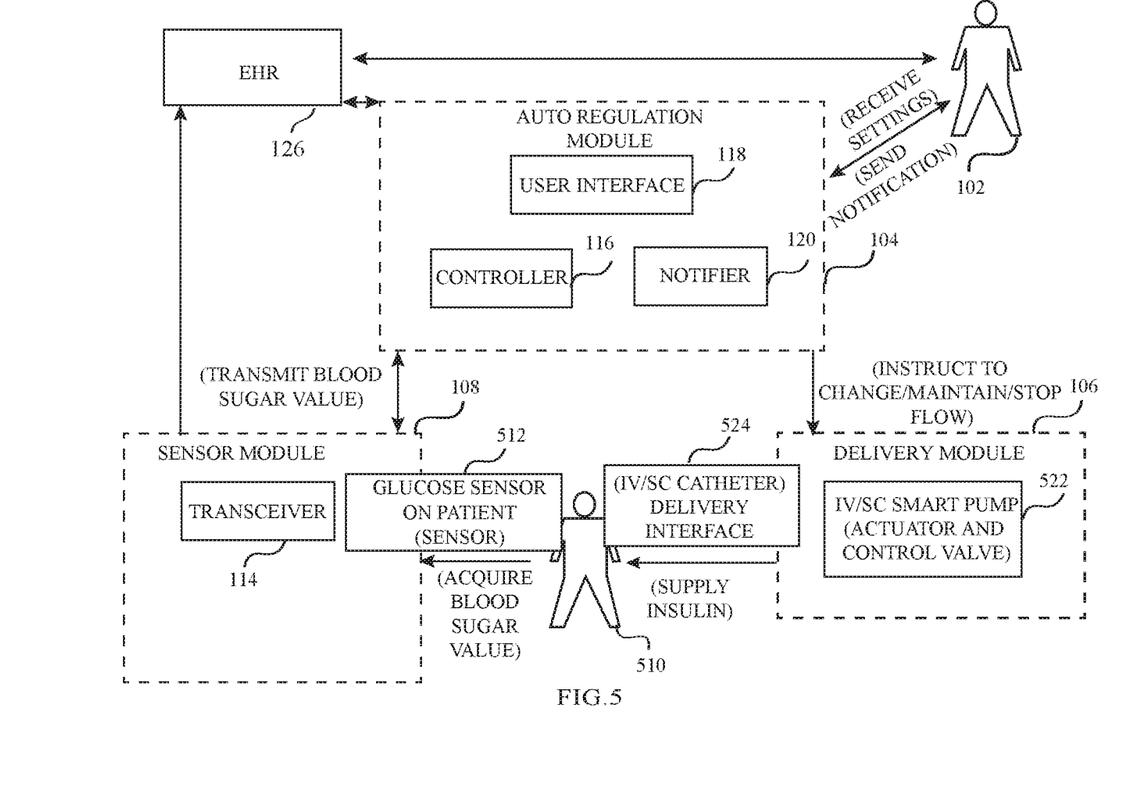
FIG. 5 depicts an automated regulation system designed to monitor and alter a patient's vital levels, specifically the patient's blood glucose levels, to achieve an artificial homeostasis by creating an automated feedback loop, in accordance with an embodiment of the present invention.

FIG. 5 similarly provides an example of system 100, in an embodiment in which system 100 is employed to treat a patient suffering from diabetic ketoacidosis. A state of insulin deficiency causes high blood glucose (BG) levels and a breakdown of normal bodily feedback processes that auto-regulate glucose metabolism in human and/or animal cells. These normal bodily feedback processes can be replaced or supplemented with an artificial feedback loop, as shown in FIG. 5. As discussed above, care provider 102 can access the medical record of patient 510, who is suffering from the effects of diabetic ketoacidosis, by care provider 102 accessing the EHR 126 or auto-regulation module 104. In order to auto-regulate intravenous (IV) or subcutaneous (SC) insulin drip administered through delivery interface 124, the blood glucose levels of patient 510 are monitored using a venous or subcutaneous biosensor 512, or other similar sensor. Transceiver 114 of sensor module 108 transmits the measured glucose level values to auto-regulation module 104. In auto-regulation module 104, based on the default settings or customized settings input by care provider 102, controller 116 instructs delivery module 106 to deliver the required amount of insulin to patient 510.

In an embodiment of the present invention, an IV/SC smart pump 522 can be used in delivery module 106 for regulating the delivery of insulin to the patient. The feedback loop, thus provided, enables a stoppage of the insulin drip for glucose levels less than, for example, 80 mg/dL, and a resumption of the insulin drip if glucose levels rise above, for example, 140 mg/dL. A glucagon pump may also be added in parallel with smart pump 522, which can be particularly useful for measure glucose levels of less than, for example, 50 mg/dL, to avoid extremely low glucose levels in patient 510. As such, patient's 510 blood glucose levels can be accurately and efficiently regulated in a medical facility or home environment, without the need to frequently prick the patient's finger or without the need for a care provider to manually re-adjust the insulin drip flow rate at regular intervals.

Figure 6:
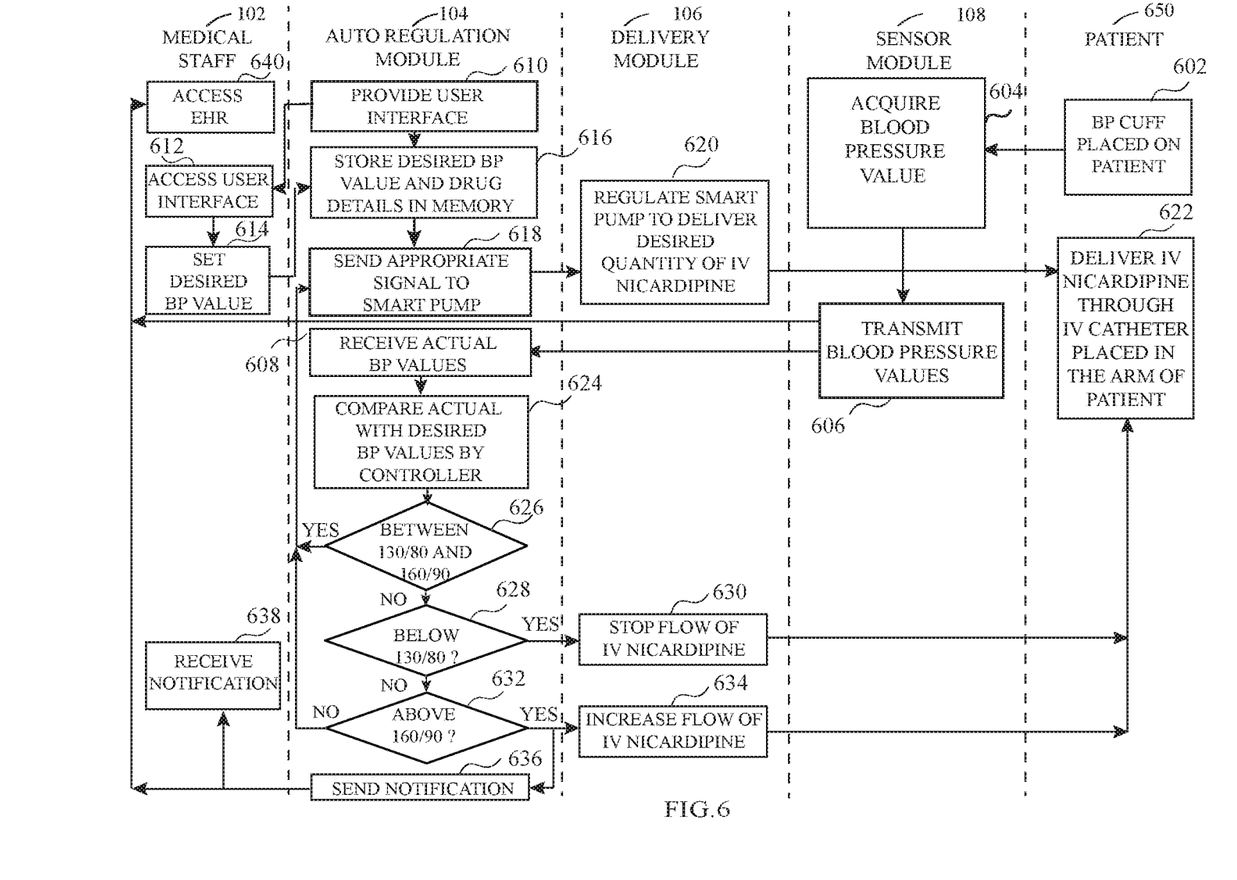
FIG. 6 depicts a process flow diagram depicting a method of automatically regulating a patient's blood pressure levels, in accordance with an embodiment of the present invention.

FIG. 6 provides an example of system 100 used to monitor and alter the blood pressure of patient 650, who, in the example provided in FIG. 6, suffers from high blood pressure (or conditions associated with the effects of high blood pressure, such as subarachnoid hemorrhage or stroke).

To treat patient 650, system 100 aims to lower the patient's blood pressure to a manageable and/or healthy level, which is the target level. The lowering of the patient's blood pressure should be done efficiently but also safely, and so the goal is to slowly lower the patient's blood pressure to the target level, for example, <160/90 mmHg, thereby improving perfusion to the brain and restoring motor functions.

In step 602, a blood pressure (BP) sensing device is used on patient 650 to acquire BP values by sensor module 108, as shown in step 604. In step 606, transceiver 114 of sensor module 108 transmits the measured BP values to auto-regulation module 104. In step 640, care provider 102 treating patient 650 can access the EHR 126 to read the medical records of patient 650, and to access user interface 118 of auto-regulation module 104 in step 612 via an interface provied during step 610. During step 614, care provider 102 can enter a target BP level which is to be achieved for patient 650, as well as the details of the therapeutics and initial dosages to be administered to patient 650—these levels and dosages are stored in auto-regulation module 104. Alternatively, the target BP levels, therapeutics, and dosages can be predetermined from a database or determined by an AI component of system 100, based on the patient's baseline levels or other clinical guidelines. These values are stored during step 616.

In the example shown in FIG. 6, patient 650 receives IV Nicardipine at the rate of 5 mg/hour, as shown in step 622, through an IV catheter placed on the patient 650. The IV catheter is an example of delivery interface 124, and is a component of delivery module 106. Auto-regulation module 104 instructs delivery module 106 to regulate the flow of IV Nicardipine administered to patient 650, as shown in step 618, in line with the target levels either set by care giver 102 or an AI component of system 100, or otherwise predetermined by auto-regulation module 104 of EHR 126. The smart pump of delivery module 106 adjusts the flow of IV Nicardipine in step 620. Upon receiving the actual BP level of patient 650, as measured by the BP monitor of sensor module 108 during step 608, controller 116 compares the measured levels with the target values during step 624. If controller 116 determines, during step 626, that the measured BP levels are between, for example, 130/80 and 160/90 mmHg, then controller 116 instructs delivery module 106 to continue the IV Nicardipine supply at a steady rate to maintain or lower BP levels which remain slightly elevated. Similarly, if controller 116 determines, during step 628, that the BP values are below, for example, 130/80 mmHg, controller 116 instructs delivery module 106 to decrease or cease the IV Nicardipine flow during step 630. If controller 116 determines that the BP values are above, for example, 160/90 mmHg, during step 632, the flow of IV Nicardipine is increased during step 634, by 2.5 mg/hr increments, for example, until the target BP range is reached. The frequency of BP value acquisition by sensor module 108 can be raised or lowered depending on the results achieved—for example, if patient 650 has extremely high blood pressure levels, system 100 can increase the frequency of BP levels measured by sensor module 108. If patient 650 has stable and lower blood pressure levels, system 100 can decrease the frequency of BP levels measured by sensor module 108. The system also sends notification, during step 636, and updates the EHR 126 with the latest results in real-time. The notifications can be received by care provider 102, or other personnel, during step 638.

As shown in the non-exhaustive discussion of the examples above, system 100 can be utilized to continuously or periodically measure patient inputs or vital signs via sensor module 108, including, but not limited to: blood pressure; heart rate; temperature; weight; oxygen saturations; lab variables from venous, arterial blood; body fluids, such as saliva, tears, sweat, peritoneal fluid, or urine; glucose levels; sodium levels; potassium levels; arterial blood gases (ABG); pH levels; oxygen levels, carbon dioxide levels; bicarbonate levels; PT/INR (prothrombin time/international normalized ratio values used to calculate and measure blood clotting); activated partial thromboplastin time (aPTT); specific gravity; osmolality; levels of therapeutics or other chemicals detected in a patient, such as beta natriuretic peptide, dopamine, vancomycin; heparin, hormones; and other similar levels. Moreover, by using a variety of biosensors or microassay chips within sensor module 108, telemetry devices attached to the patient's body to obtain and electronically transmit measured levels to a smart programmable delivery system, such as auto-regulation module 104, as well as to the EHR 126, helps create the feedback loop needed to automatically control the future rate of flow or dose of medication to delivery module 106. The above levels can be measured by one or more sensors; it is contemplated that a plurality of biosensors can be combined on a singular sensor coupled to the patient's body, either directly or indirectly, to measure one or more of the above-discussed levels, thereby simplifying the sensor process within a medical facility or home environment.

With the help of the present invention it will be possible to use various inputs from biosensors and EHR lab values and feed the inputs back into the decision-making cascades using software and programmable pumps to auto-regulate the flow of various kinds of titratable drug, fluids, gases or medicines. As such, the delivery and dosing of anesthesia medications, asthma and chronic obstructive pulmonary disease (COPD) medications, congestive heart failure (CHF) medications, blood pressure medications, blood thinners, insulin and other hormones, oxytocin, antibiotics, diuretics, immunotherapy, chemotherapy, patient controlled anesthesia (PCA), oral medications such as coumadin and levothyroxine can also be auto-regulated by this system and method to save time and resources, while increasing patient compliance and safety. Moreover, ventilators, BiPAP/CPAP, peritoneal dialysis, and hemodialysis machines can also be optimized by using this method.

Table 1 below shows non-exhaustive examples of the system and method of the present invention used to generate artificial homeostasis by creating the feedback loops discussed in detail above:

TABLE 1

| Disease/Treatment | Measured Value/ Biosensor Output | Feedback connection to Controller | Inpatient/EMS/ Ambulatory use |
|---|---|---|---|
| Dehydration/ Volume loss/ PostOp/0.9% Normal Saline (NS) drip | Blood Pressure (BP) | BP-wired or wireless to EHR | All situations. |
| Diabetic Ketoacidosis or uncontrolled Diabetes/ IV or SC Insulin/Glucagon | Blood Glucose | SC Glucose via Bluetooth/ Fingerstick glucose to EHR | All situations. |
| Arterial or Vein Thrombosis/ IV Heparin drip | aPTT (activated partial thromboplastin time) | Lab to EHR | All situations. |
| Acidosis/IV 0.9% NS with Sodium Bicarbonate drip | pH, HCO3-from Arterial Blood Gases (ABG) | Lab to EHR | All situations. |
| Shortness of breath/ Oxygen gas/ Nebulizer meds | Finger Pulse Oximetry or ABG and/or spirometry | wired/lab to EHR | All situations. |
| Low Sodium levels/ Low Potassium levels/IV 0.9% NS or KCl drip | Na+/K+ | Lab to EHR | Inpatient |
| Severe High BP/stroke/ Subarachnoid Hemorrhage/IV Nicardipine drip | BP monitor | BP-wired, connects to EHR | Inpatient. |
| Hypercoagulable state/ Oral Coumadin | INR monitor | LCD/fax to EHR | Outpatient |
| Severe infection/IV Vancomycin | S. Vancomycin level | Lab to EHR | All situations. |

While Table 1 includes examples of various conditions, measured patient levels, and feedback mechanisms, it is appreciated that the system can be used with other patient levels and treatments for other conditions, so long as the level can be altered by the increasing/decreasing of an amount of one or more therapeutics delivered to the patient to achieve an artificial homeostasis.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An automatic regulation system for achieving a target vital level in a patient, the system comprising:

an auto-regulation module including an electronic health record existing on an electronic device including a memory, a signal transmitter, and a signal receiver, the electronic health record configured to store a plurality of target vital levels for a patient, the plurality of target vital levels including at least two levels selected from the group consisting of heart rate, blood pressure, temperature, oxygen saturation, blood glucose, pH, sodium, potassium, and bicarbonate, the auto-regulation module in electronic communication with each of a delivery module and a sensor module, and the electronic health record configured to automaticallly update and transmit an instruction to the delivery module based on a received value from the sensor module;

the delivery module couplable to the patient and including a signal receiver and a delivery device, such that the delivery module signal receiver receives a signal from the auto-regulation module including the electronic health record, the signal adapted to provide the instruction to deliver a calculated amount of a therapeutic to the patient via the delivery device, the calculated amount of the therapeutic administered to alter at least one of a plurality of measured vital levels for the patient, and the calculated amount of the therapeutic being automatically updated by the electronic health record, the plurality of measured vital levels including at least two levels selected from the group consisting of heart rate, blood pressure, temperature, oxygen saturation, blood glucose, pH, sodium, potassium, and bicarbonate;

the sensor module couplable to the patient and including a signal transmitter and a plurality of sensing components, such that each of the plurality of sensing components is adapted to detect at least one of the measured vital levels for the patient, and such that the signal transmitter is adapted to send the detected at least one of the measured vital levels to the auto-regulation module signal receiver including the electronic health record;

wherein the auto-regulation module receives the detected at least one of the measured vital levels from the sensor module, compares, via the electronic health record, the detected at least one of the measured vital levels to a matching one of the plurality of target vital levels stored in the memory that is in communication with the electronic health record, and updates, via the electronic health record, the signal sent to the delivery module signal receiver to update the amount of the therapeutic adapted to be administered to the patient via the delivery device, such that a closed feedback loop is created between the auto-regulation module including the electronic health record, the delivery module, and the sensor module, and such that an artificial homeostasis is created via the automatic regulation system.

2. The automatic regulation system of claim 1, wherein one of the plurality of target vital levels is an oxygen saturation level for the patient, further comprising a cannula adapted to be coupled to the patient, the cannula being a part of the delivery module and adapted to supply oxygen to the patient to alter the patient's oxygen saturation level.

3. The automatic regulation system of claim 2, wherein one of the plurality of sensing components of the sensor module is a pulse oximeter adapted to measure the patient's oxygen saturation level, the pulse oximeter electronically coupled to the sensor module signal transmitter which transmits the measured oxygen saturation level to the auto-regulation module.

4. The automatic regulation system of claim 1, wherein one of the plurality of target vital levels is a blood pressure level for the patient, further comprising a blood pressure monitor coupled to the patient, the blood pressure monitor being a part of the sensor module and designed to measure the patient's blood pressure.

5. The automatic regulation system of claim 4, further comprising an intravenous catheter coupled to the patient, the intravenous catheter being a part of the delivery module and adapted to supply the amount of the therapeutic to the patient to match the measured blood pressure level with the target blood pressure level.

6. The automatic regulation system of claim 5, wherein the therapeutic is nicardipine, and the auto-regulation module determines the amount of the nicardipine necessary to equate the measured blood pressure level with the target blood pressure level.

7. The automatic regulation system of claim 1, wherein the delivery module further comprises a nebulizer adapted to administer the amount of the therapeutic to the patient.

8. The automatic regulation system of claim 7, wherein the nebulizer is in wireless communication with the auto-regulation module, wherein the auto-regulation module wirelessly transmits an instruction to the nebulizer to administer the amount of the therapeutic to the patient when the sensor module detects that one of the plurality of measured vital levels differs from a matching one of the plurality of target vital levels.

* * * * *